US012642761B2

(12) United States Patent
Thakur et al.

(10) Patent No.: US 12,642,761 B2
(45) Date of Patent: *Jun. 2, 2026

(54) OCULAR COMPOSITIONS

(71) Applicant: RE-VANA THERAPEUTICS LTD, Belfast (GB)

(72) Inventors: Raghu Raj Singh Thakur, Belfast (GB); David Jones, Newtownabbey (GB); Rahul Sonawane, Belfast (GB); Yujing Wang, Belfast (GB); Karim Soliman, Hamilton (CA)

(73) Assignee: Re-Vana Therapeutics Ltd., Belfast (GB)

( * ) Notice: Subject to any disclaimer, the term of this patent is extended or adjusted under 35 U.S.C. 154(b) by 715 days.

This patent is subject to a terminal disclaimer.

(21) Appl. No.: 17/414,958

(22) PCT Filed: Dec. 20, 2019

(86) PCT No.: PCT/EP2019/086829
§ 371 (c)(1),
(2) Date: Jun. 17, 2021

(87) PCT Pub. No.: WO2020/128062
PCT Pub. Date: Jun. 25, 2020

(65) Prior Publication Data
US 2022/0054407 A1 Feb. 24, 2022

(30) Foreign Application Priority Data
Dec. 21, 2018 (EP) .................................... 18215025

(51) Int. Cl.
*A61K 9/00* (2006.01)
*A61K 39/00* (2006.01)
(Continued)

(52) U.S. Cl.
CPC ............ *A61K 9/0051* (2013.01); *A61K 45/06* (2013.01); *A61K 47/32* (2013.01); *A61K 47/34* (2013.01)

(58) Field of Classification Search
None
See application file for complete search history.

(56) References Cited

U.S. PATENT DOCUMENTS 6,974,591 B2 * 12/2005 Kendrup ................ A61K 9/282
424/475
2018/0325812 A1 11/2018 Thakur et al.

FOREIGN PATENT DOCUMENTS

JP 2018532563 A 11/2018
WO WO-2017015616 A1 * 1/2017 ............. A61K 38/18
(Continued)

OTHER PUBLICATIONS

Celike al., "Complications of dexamethasone implants: risk factors, prevention, and clinical management", Complications of dexamethasone implants, Int. J Ophthalmol, vol. 13. No. 10, Oct. 18, 2020. (Year: 2020).*
(Continued)

*Primary Examiner* — Kyung S Chang
(74) *Attorney, Agent, or Firm* — Barnes & Thornburg LLP; Aisha R. Hasan; Anusuya Das

(57) ABSTRACT
The present invention relates to ocular compositions for the controlled release of a therapeutic agent. The ocular composition comprises at least 20% w/w of a therapeutic agent; 5 to 75% w/w of a photopolymerizable composition selected from the group consisting of fragments or monomers of polyalkylene glycol mono-acrylate, polyalkylene glycol diacrylate, polyalkylene glycol methacrylate and polyalkylene glycol dimethacrylate, and mixtures, copolymers, and block copolymers thereof; 0.1 to 40% w/w of a biodegradable polymer selected from the group consisting of lactide/
(Continued)

glycolide copolymer (including poly(lactide-co-glycolide) (PLGA)), poly (L-lactide) (PLA), polyhydroxyalkanoates, including polyhydroxybutyrate, polyglycolic acid (PGA), polycaprolactone (PCL), poly (DL-lactide) (PDL), poly (D-lactide), lactide/caprolactone copolymer, poly-L-lactide-co-caprolactone (PLC) and mixtures, copolymers, and block copolymers thereof; and a photoinitiator.

11 Claims, 8 Drawing Sheets

(51) Int. Cl.

| | | |
|---|---|---|
| *A61K 45/06* | (2006.01) | |
| *A61K 47/32* | (2006.01) | |
| *A61K 47/34* | (2017.01) | |
| *A61P 27/00* | (2006.01) | |
| *A61P 27/02* | (2006.01) | |
| *C07K 16/22* | (2006.01) | |

(56) References Cited

FOREIGN PATENT DOCUMENTS

| WO | 2017081154 A1 | 5/2017 |
|---|---|---|
| WO | 2018206749 A1 | 11/2018 |

OTHER PUBLICATIONS

Written Opinion of the International Application PCT/EP2019/066829, Apr. 7, 2020, 7 pages.

Mcavoy, Kathryn , et al., "Synthesis and Characterisation of Photocrosslinked poly(ethylene glycol) diacrylate Implants for Sustained Ocular Drug Delivery", Pharmaceutical Research 35: 36, 2018, pp. 1-17.

Huang, Xiao, "On the importance and mechanisms of burst release in matrix-controlled drug delivery systems." Journal of controlled release 73.2-3 (2001): 121-136.

* cited by examiner

OCULAR COMPOSITIONS

CROSS REFERENCE TO RELATED APPLICATIONS

This application is a United States National Stage Application filed under 35 U.S.C. § 371 claiming the benefit of PCT Application No. PCT/EP2019/086829, filed on Dec. 20, 2019, which claims priority to and the benefit of European Application No. 18215025.0, filed on Dec. 21, 2018, all of which are incorporated herein by reference in their entireties.

DESCRIPTION

Field of the Invention

The present invention relates to ocular compositions and ocular implants for the controlled release of a therapeutic agent.

Background of the Invention

Chronic retinal diseases are the leading contributor to visual impairment and blindness worldwide. Loss of sight has a major personal impact on people's daily lives and has a profound economic impact on individuals, families, public health and society. The World Health Organization estimates that globally about 285 million people are visually impaired, of which 39 million are blind and 246 million have low vision. Diseases that originate in the posterior segment (PS) or back of the eye lead to permanent loss of vision if left untreated and account for most of the blindness, such as in age-related macular degeneration (AMD), diabetic retinopathy (DR), diabetic macular edema (DME), cytomegalovirus (CMV) retinitis, retinitis pigmentosa, uveitis and glaucoma. The PS of the eye, which includes the retina, choroid, and vitreous body, is difficult to access due to the recessed location within the orbital cavity. Therefore, delivery of therapeutic agents to the PS of the eye has remained one of the most challenging tasks for pharmaceutical scientists and retina specialists.

Multiple approaches have been used to deliver therapeutic agents to the PS of the eye such as systemic, topical, periocular (or transscleral) and intravitreal. Topical (e.g. eye drops) and systemic (e.g. oral tablets) routes result in low or sub-therapeutic agent levels due to multiple ocular barriers, requiring administration of unnecessarily high concentrations of therapeutic agent that causes therapeutic agent-related toxicity and producing low treatment efficacy.

WO2017081154A1 discloses ocular compositions that can be administered to the eye in various forms to achieve controlled release of a therapeutic agent. These compositions can be used to form ocular implants by crosslinking the formulation either in situ after injecting it into the eye of a patient or can be preformed prior to injecting in the eye.

There is a need for alternative systems for ocular delivery of therapeutic agents.

SUMMARY OF THE INVENTION

In a first aspect, the invention relates to an ocular composition that can be administered to the eye in various forms to achieve controlled release of a therapeutic agent. Such ocular composition comprises:

a) at least 20% w/w of a therapeutic agent;

b) 5 to 75% w/w of a photopolymerizable composition selected from the group consisting of fragments or monomers of polyalkylene glycol mono-acrylate, polyalkylene glycol diacrylate, polyalkylene glycol methacrylate, polyalkylene glycol dimethacrylate and mixtures, copolymers and block copolymers thereof;

c) 0.1 to 40% w/w of a biodegradable polymer selected from the group consisting of lactide/glycolide copolymer (including poly(lactide-co-glycolide) (PLGA)), poly (L-lactide) (PLA), polyhydroxyalkanoates, including polyhydroxybutyrate, polyglycolic acid (PGA), polycaprolactone (PCL), poly (DL-lactide) (PDL), poly (D-lactide), lactide/caprolactone copolymer, poly-L-lactide-co-caprolactone (PLC) and mixtures, copolymers, and block copolymers thereof; and d) a photoinitiator.

In a further aspect, the invention relates to a method of making the above ocular composition.

In a still further aspect, the present invention relates to the above ocular composition for use in the preparation of an ocular implant.

In a still further aspect, the present invention relates to a method for making such ocular implant.

In a still further aspect, the present invention relates to an ocular implant obtainable by such method.

In a still further aspect, the present invention relates to an ocular implant comprising at least 20% w/w of a therapeutic agent, 5 to 75% w/w of a crosslinked polymer matrix and 0.1 to 40% w/w of a biodegradable polymer selected from the group consisting of lactide/glycolide copolymer (including poly(lactide-co-glycolide) (PLGA)), poly (L-lactide) (PLA), polyhydroxyalkanoates, including polyhydroxybutyrate, polyglycolic acid (PGA), polycaprolactone (PCL), poly (DL-lactide) (PDL), poly (D-lactide), lactide/caprolactone copolymer, poly-L-lactide-co-caprolactone (PLC) and mixtures, copolymers, and block copolymers thereof; characterized in that:

a) the crosslinked polymer matrix is obtained by crosslinking a photopolymerizable composition selected from the group consisting of fragments or monomers of polyalkylene glycol mono-acrylate, polyalkylene glycol diacrylate, polyalkylene glycol methacrylate, polyalkylene glycol dimethacrylate and mixtures, copolymers and block copolymers thereof;

b) the therapeutic agent and the biodegradable polymer are embedded in the crosslinked polymer matrix.

The present invention provides ocular compositions and implants that can be administered to the eye in various forms to achieve controlled release of a therapeutic agent.

The invention allows the flexibility to administer a range of small and large therapeutic molecules including proteins, peptides and gene therapeutics, and maintain their activity for a controlled period of time.

The ocular compositions and implants according to the present invention enable to include amounts of therapeutic agent equal or greater than 20% w/w, thus enabling the manufacture of high loaded therapeutic delivery implants without facing unacceptable burst releases. Furthermore, the overall size of the implants of the present invention can be substantially reduced without compromising the efficacy of the therapeutic agent release profile over prolonged periods of time. In view of the reduced sizes, patient acceptance, tolerability and comfort are overall and generally improved.

The high concentration of therapeutic agent in the ocular compositions and implants of the present invention enables also to increase the bioavailability of the therapeutic agent itself, thus ensuring the efficacy of the treatment over the entire period of time.

Furthermore, implants with reduced dimensions and high drug loading allow administration via narrow gauge needles causing low ocular tissue trauma.

DETAILED DESCRIPTION OF THE INVENTION

Figure 1:
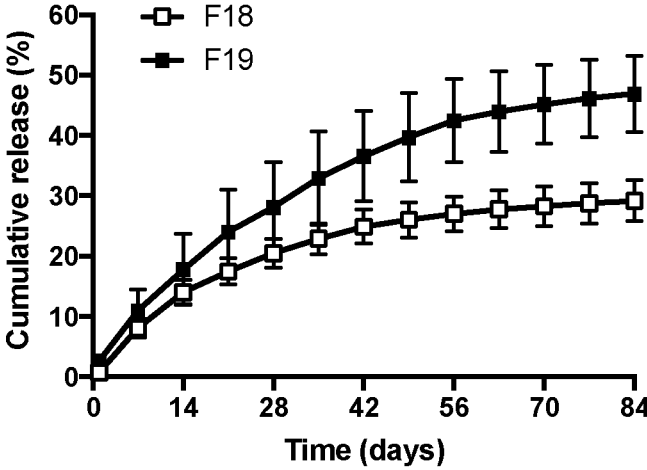
FIG. 1 Shows the in vitro release of BEZ from implants F18 and F19, expressed as percentage cumulative release (Mean±SD, n=3).

As used herein, the term "% w/w" means the weight percentage of a given component over the total weight of the copolymer, the composition or the implant including such component, as the case may be.

As used herein, "biodegradable" is the chemical degradation by biological means. In some embodiments, the biodegradation is 100%, 98%, 90%, 85%, 80%, 60%, 50%, or 45% degradation of one or more of the compositions, monomers, oligomers, fragments, polymers, photoinitiators, solvents, co-solvents, or co-initiators.

As used herein "copolymer" is a mixture of two or more different types of monomer units. As used herein "block copolymer" is a mixture of two or more homopolymer subunits.

The therapeutic agent of the composition of the present invention can be selected from a wide range of small and large molecules. Exemplary therapeutic agents include, but are not limited to, polypeptides, nucleic acids, such as DNA, RNA, and siRNA, growth factors, steroid agents, antibody therapies, antimicrobial agents, antibiotics, antiretroviral therapeutic agents, anti-inflammatory compounds, antitumor agents, anti-angiogeneic agents, anti-VEGF (Vascular endothelial growth factor) agents and chemotherapeutic agents.

In one embodiment, the therapeutic agent of the present invention includes, but is not limited to, ketorolac, naphazoline, lidocaine, bevacizumab, aflibercept, pegaptanib, brimonidine tartrate, dorzolamide, bromfenac sodium, azithromycin, rapamycin, bepotastine besilate, diclofenac, besifloxacin, cysteamine hydrochloride, fluocinolone acetonide, difluprednate, tasimelteon, ocriplasmin, enoxaparin sodium, ranibizumab, latanoprost, timolol maleate, bimatoprost, ofloxacin, cephazolin, phenylephrine, dexamethasone, triamcinolone acetonide, levofloxacin, cyclophosphamide, melphalan cyclosporine, methotrexate, azathioprine, travoprost, verteporfin, tafluprost, ketotifen fumarate, foscarnet, amphotericin B, fluconazole, voriconazole, ganciclovir, acyclovir, gatifloxacin, mitomycin-C, prednisolone, prednisone, vitamin (vitamin A, vitamin C, and vitamin E), zinc, copper, lutein, zeaxanthin or combinations thereof.

In another embodiment, the therapeutic agent of the present invention is dexamethasone, timolol maleate, brimonidine tartrate, triamcinolone acetonide, bromfenac sodium, latanoprost or mixtures thereof.

In one embodiment, the compositions or implants of the present invention can deliver bioactive agents, a large molecular weight therapeutic agent, such as, aflibercept, pegaptanib, or an antibody therapeutic, such as ranibizumab, bevacizumab, trastuzumab, rituximab, gentuzumab, ozagamicin, brolucizumab or cetuximab.

In some embodiments, the molecular weight of the therapeutic agent is greater than 200 Da, 500 Da, 1000 Da, 10 kDa, 30 kDa, 50 kDa, 75 kDa, 100 kDa, 150 kDa, 200 kDa and 250 kDa.

According to other embodiments of the present invention, the therapeutic agent is present in an amount between 20 and 70% w/w, between 30 and 70% w/w, between 40 and 70% w/w and between 50 and 70% w/w of the total weight of the ocular composition.

The therapeutic agent can be used as such or in form of a solution wherein an amount of therapeutic agent is dissolved in a suitable solvent. The therapeutic agent can also be freeze-dried or spray-dried before being used in the preparation of the ocular composition of the present invention in order to facilitate the incorporation of high concentrations of the therapeutic agent into the implant. The amount of the therapeutic agent to be dissolved depends on the final loading that the ocular composition or implant has to have. The choice of the solvent depends on the polarity of the therapeutic agent.

According to an embodiment of the present invention, the solvent can be selected from water, dimethyl sulfoxide, decylmethyl sulfoxide, 2-pyrrolidone, 1-methyl-2-pyrrolidone, N-vinyl-pyrrolidine, N-Methyl-2-pyrrolidone, N-ethyl-pyrrolidone, glycerol formal, glycerol, polyethylene glycol, propylene glycol, benzyl alcohol, benzyl benzoate, ethyl benzoate, triacetin, triethyl citrate, dimethylformamide, dimethylacetamide and tetrahydrofuran.

In one embodiment, co-solvents may be used and they can be selected from dichloromethane, tetrahydrofuran, ethyl acetate, acetone, dimethylformamide, acetonitrile, acetic acid, methanol, ethanol, isopropanol, glycofurol or butanol.

In case of hydrophilic therapeutic agents, the solvent may be an aqueous based solvent such as water or a phosphate buffered saline (PBS) solution.

According to another embodiment, the solvent may be selected from dimethyl sulfoxide, decylmethyl sulfoxide, 2-pyrrolidone, 1-methyl-2-pyrrolidne, N-methyl-2-pyrrolidone and glycerol formal.

Furthermore, the above described solvents and co-solvents can be used in the preparation of any of the compositions and implants of the invention, in combination with any of the other photopolymerizable compositions, biodegradable polymers, photoinitiators, pore forming agents, and co-initiators described herein.

In one embodiment, a solvent is used when the biodegradable polymer is PLGA, PCL, PLC and/or PLA. In one embodiment the solvent is N-Methyl-2-pyrrolidone and N-Vinyl-2-pyrrolidine when the biodegradable polymer is PLGA, PCL, PLC and/or PLA. In another embodiment, a solvent is used when the photopolymerizable composition is PEGDA.

The photopolymerizable fragments or monomers of the present invention can be used in any of the compositions and implants of the invention in combination with any of the other biodegradable polymers, therapeutic agents, photoinitiators, solvents, co-solvents, drug modulating agents and co-initiators described herein or known in the common general knowledge.

In one embodiment, the photopolymerizable composition of the invention can be biodegradable. In some embodiments the biodegradation takes place over 1 minute, 10 minutes, 20 minutes, 2 hours, 6 hours, 12 hours, 24 hours, 2 days, 5 days, 1 week, 1 month, 2 months, 5 months, 6 months, 8 months or 12 months. In some embodiments the biodegradation takes place between 1 month and 12 months, between 6 months and 12 months, or between 8 months and 12 months.

As used herein, the term "photopolymerizable composition" is a composition which can form a crosslinked polymer network upon exposure to light, in particular UV light. As used herein, photopolymerizable compositions include photopolymerizable monomers and oligomers (such as, dimers, trimers, and tetramers). The terms "oligomers" and "fragments" can be used interchangeably to mean between two and twenty monomers, optionally between two and ten monomers, further optionally between two and five monomers or between two and four monomers. A "photopolymerizable monomer" is a single unit of a photopolymerizable polymer that can bind chemically to other monomers to form a polymer.

Photopolymerizable compositions of the present invention can be crosslinked with UV radiation to form the crosslinked polymer matrix of the ocular implant of the present invention.

In one embodiment, the photopolymerizable composition is selected from the group consisting of fragments or monomers of polyalkylene glycol mono-acrylate, polyalkylene glycol diacrylate, polyalkylene glycol methacrylate, polyalkylene glycol dimethacrylate, and mixtures, copolymers, and block copolymers thereof.

In one embodiment, the photopolymerizable compositions are polyalkylene glycol diacrylate fragments or monomers incorporating diacrylate end units selected from the group comprising polyether fragments or monomers, polyester fragments or monomers, polycarbonate fragments or monomers or mixtures, copolymers, or block copolymers thereof.

In one embodiment, the photopolymerizable composition comprises monomers incorporating diacrylate end units, such as 4-arm or 8-arm PEG acrylate.

In another embodiment, the photopolymerizable composition is polyethylene glycol diacrylate, diethylene glycol diacrylate, polyethylene glycol dimethacrylate, diethylene glycol dimethacrylate, polypropylene glycol diacrylate, dipropylene glycol diacrylate, dipropylene glycol dimethacrylate and polypropylene glycol dimethacrylate or mixtures, copolymers, or block copolymers thereof.

In another embodiment, the photopolymerizable composition is polyethylene glycol diacrylate (PEGDA), polyethylene glycol mono-acrylate (PEGMoA) or polyethylene glycol dimethacrylate (PEGDMA).

In yet another embodiment, the photopolymerizable composition is polyethylene glycol diacrylate (PEGDA).

In yet another embodiment, the photopolymerizable composition is polyethylene glycol methacrylate (PEGMA) or mixtures of PEGMA with other polyalkylene glycol mono-acrylates, diacrylates, methacrylates and/or dimethacrylates. In an embodiment, the polymerizable composition is a mixture of PEGDA, PEGMoA and/or PEGMA.

PEGDA is a synthetic polymer, available in different molecular weights. PEGDA is extremely amenable to mechanical, structural and chemical alteration and so resulting in hydrogels with variable properties in terms of drug delivery and other biomedical applications. PEGDA is formed through the functionalization of the end of each PEG molecule with an acrylate group. PEGDA is also non-toxic, eliciting only a minimal immunogenic response. PEGDA has double-bond containing acrylate end groups which show rapid polymerization when exposed to light in the presence of an appropriate initiator to produce a hydrogel network.

The average molecular weight of the photopolymerizable compositions of the present invention is typically between 100 and 300,000 Da, between 200 to 100,000 Da, between 200 to 50,000 Da, between 200 to 20,000 Da, between 200 to 10,000 Da, between 200 and 8,000 Da, between 200 and 5,000 Da, or between 200 and 1,000 Da.

It has been found, for the compositions and implants of the present invention, that an increase in molecular weight of the photopolymerizable compositions results in an increase in therapeutic agent release rate. Without wishing to be bound by theory, it is believed that photopolymerizable compositions with lower molecular weights have higher crosslinking density and therefore slower therapeutic agent release rates.

The photopolymerizable compositions of the present invention typically have viscosities between 0.1 to 7 dL/g, between 0.2 to 5 dL/g, or between 0.5 to 2 dL/g.

In an embodiment, the photopolymerizable composition is present in an amount between 10 and 75% w/w, between 20 and 75 w/w, between 30 and 75% w/w, between 40 and 75% w/w and between 45 and 75% w/w.

The biodegradable polymers of the present invention can be used in any of the compositions and implants of the invention in combination with any of the other photopolymerizable compositions, therapeutic agents, photoinitiators, solvents, co-solvents, therapeutic agent release modulating agents and co-initiators described herein or known in the common general knowledge.

The biodegradable polymers of the present invention are biodegradable but not photopolymerizable.

In one embodiment of the present invention, the biodegradable polymers are aliphatic polyester-based polyurethanes, polylactides, polycaprolactones, polyorthoesters or mixtures, copolymers, or block copolymers thereof.

In another embodiment of the present invention, the biodegradable polymer is chitosan, poly(propylene fumarate), lactide/glycolide copolymer (PLGA), poly (L-lactide) (PLA), polyglycolic acid (PGA), polycaprolactone (PCL), lactide/caprolactone copolymer (PLC), polyhydroxybutyrate, natural biodegradable polymers, such as collagen and hyaluronic acid, or mixtures, copolymers, or block copolymers thereof.

In another embodiment, the biodegradable polymer is selected from the group consisting of lactide/glycolide copolymer (including poly(lactide-co-glycolide) (PLGA)), poly (L-lactide) (PLA), polyhydroxyalkanoates, including polyhydroxybutyrate, polyglycolic acid (PGA), polycaprolactone (PCL), poly (DL-lactide) (PDL), poly (D-lactide), lactide/caprolactone copolymer, poly-L-lactide-co-caprolactone (PLC) and mixtures, copolymers, and block copolymers thereof.

In one embodiment, the biodegradable polymer is lactide/glycolide copolymer (including poly(L-lactide-co-glycolide) (PLGA)), poly (L-lactide) (PLA), poly(DL-lactide) (PDL), and lactide/caprolactone copolymer (PLC).

In a particular embodiment, the biodegradable polymer is poly(lactide-co-glycolide) (PLGA).

PLGA is typically prepared by polymerization of lactic acid and glycolic acid monomers. The glass transition temperatures (Tg) of PLGA copolymers are above physiological temperatures of 37° C., which imparts a moderately rigid chain configuration and therefore the mechanical strength at ambient temperatures. The use of PLGA in different lactide (LA) to glycolide (GA) ratio and molecular weights allows different drug release profiles. An increase in GA content will result in an increased water uptake of PLGA and therefore more rapid degradation. The degradation of PLGA with LA/GA 50/50 is typically between one and three months. In one embodiment, the molar ratio of lactic acid to glycolic acid in the PLGA is 90% lactic acid to 10% glycolic acid, 85% lactic acid to 15% glycolic acid, 75% lactic acid to 25% glycolic acid, 65% lactic acid to 35% glycolic acid, 50% lactic acid to 50% glycolic acid, 35% lactic acid to 65% glycolic acid, 25% lactic acid to 75% glycolic acid, 15% lactic acid to 85% glycolic acid, and 10% lactic acid to 90% glycolic acid.

In another embodiment, the biodegradable polymer is PCL, PLC, PLA, or mixtures, copolymers, or block copolymers thereof.

In an embodiment, the biodegradable polymer is present in an amount between 1 and 40% w/w, between 1 and 30% w/w, between 1 and 20% w/w, between 2 and 10% w/w, between 5 and 10% w/w.

The photoinitiators described herein can be used in any of the compositions and implants of the present invention in combination with any of the other photopolymerizable compositions, biodegradable polymers, therapeutic agents, photoinitiators, solvents, co-solvents, and co-initiators described herein.

In certain embodiments, the photoinitiator is designed to work using light from 200 to 550 nm. In some embodiments, a photoinitiator is designed to work using UV light from 200 to 500 nm. In other embodiments, a photoinitiator is designed to work using UV light from 200 to 425 nm.

In certain embodiments, the light source may allow variation of the wavelength of light and/or the intensity of the light. Light sources useful in the present invention include, but are not limited to, laser diodes and lamps. Fiber optic devices can be used to transmit the light.

In one embodiment, the photoinitiator is a ketone (i.e. RCOR'). In one embodiment, the compound is an azo compound (i.e. compounds with a —N═N— group). In one embodiment, the photoinitiator is an acylphosphineoxide. In one embodiment, the photoinitiator is a sulfur containing compound. In one embodiment, the initiator is a quinone. In certain embodiments, a combination of photoinitiators is used.

In another embodiment, the photoinitiator may be selected from a hydroxyketone photoinitiator, an amino ketone photoinitiator, a hydroxy ketone/benzophenone photoinitiator, a benzyldimethyl ketal photoinitiator, a phenylglyoxylate photoinitiator, an acyl phosphine oxide photoinitiator, an acyl phosphine oxide/alpha hydroxy ketone photoinitiator, a benzophenone photoinitiator, a ribityl isoalloxazine photoinitiator, a peroxide photoinitiator, a persulfate photoinitiator or a phenylglyoxylate photoinitiator or any combination thereof. Optionally, the photoinitiator is 2-Hydroxy-4'-(2-hydroxyethoxy)-2-methylpropiophenone, 1-[4-(2-hydroxyethoxy)-phenyl]-2-hydroxy-2-methyl-1-propanone, 2,2-dimethoxy-2-phenylacetophenone (DMPA), diphenyl(2,4,6-trimethylbenzoyl) phosphine oxide (DPPO) or riboflavin. In another embodiment, the photoinitiator is benzoyl peroxide, 2,2"-azobisisobutyronitrile, dicumyl peroxide, lauroyl peroxide and/or camphorquinone.

In one embodiment, the compositions of the present invention further comprise a co-initiator. In one embodiment, the co-initiator is eosin Y, triethanolamine, camphorquinone, 1-vinyl-2 pyrrolidinone (NVP), eosin, dimethylaminobenzoate (DMAB), Irgacure® D-2959 (Sigma Aldrich, Basingstoke, UK), Irgacure® 907 (Sigma Aldrich, Basingstoke, UK), Irgacure® 651 (Sigma Aldrich, Basingstoke, UK), diphenyl (2,4,6-trimethylbenzoyl) phosphine oxide (DPPO/Darocur TPO) (Sigma Aldrich, Basingstoke, UK) or ethyl-4-N,N-dimethylaminobenzoate (4EDMAB). Optionally, the photoinitiator is riboflavin and the co-initiator is L-arginine.

In one embodiment, the composition of the present invention comprises a release modulating agent. A suitable release modulating agent may be selected in view of the specific therapeutic agent and composition of the implant, as well as the desired elution profile or release rate. The release modulating agent may be a naturally occurring agent or polymer or a synthetic agent or polymer.

All release modulating agents described herein can be used in any of the implants and compositions of the invention in combination with any of the other photopolymerizable compositions, biodegradable polymers, therapeutic agents, photoinitiators, solvents, co-solvents, and co-initiators described herein.

The release modulating agents may be present in amounts between 0.1 and 40% w/w, between 1 and 30% w/w, between 1 and 20% w/w, between 1 and 10% w/w, between 5 and 10% w/w.

Optionally, the release modulating agent alters water absorption into the implant matrix, thus controlling the release rate of the therapeutic agents and the implant degradation. In an embodiment, a suitable water absorption modulating agent is one or more polysaccharide like for example chitosan and cellulose based materials including hydroxypropyl methylcellulose (HPMC); hyaluronic acid; poloxamer; polyether like for example polyethylene glycol; gelatin; polyvinylpyrrolidone; polyvinyl alcohol and mixtures thereof. In one embodiment, suitable water absorption modulating agents are hydroxypropyl methylcellulose (HPMC) and polyethylene glycol (PEG).

In one embodiment, the release modulating agent is a pore-forming agent and/or a stability enhancing agent. Optionally, it is lactose, maltose, glucose, mannitol, sodium chloride, magnesium carbonate, magnesium hydroxide, potassium chloride, sodium bicarbonate, ammonium bicarbonate, potassium bicarbonate, agarose or sucrose.

In another embodiment, the release modulating agent is a mixture of two or more modulating agents described above, in order to provide more than one functionality to the ocular composition or implant of the present invention. Optionally, the release modulating agent is polyethylene glycol, hydroxypropyl methylcellulose (HPMC) or mixtures thereof.

Optionally, implant porosity can be adjusted by preparing implants in the presence of dispersed water-soluble porosinogens, which can be removed later by washing with water to leave an interconnected meshwork (i.e., porous hydrogels). The pore size of hydrogels prepared by the porosigen technique depends on the size of the porosinogens.

In another embodiment of the present invention, the ocular composition does not contain any release modulating agent.

Another aspect of the present invention is a method of making an ocular composition as described above. The method comprises a step of dissolving the therapeutic agent into a solvent/co-solvent to obtain a solution and, subsequently, a step of mixing, in any order of addition, the so obtained therapeutic agent solution with the polymerizable composition, the biodegradable polymer, the photoinitiator and optionally the release modulating agent. Optionally, the therapeutic agent is first mixed with the photopolymerizable composition and the so obtained mixture is mixed, in any order of addition, with the biodegradable polymer, the photoinitiator and optionally the release modulating agent. Alternatively, the therapeutic agent is first mixed with a portion of the photopolymerizable composition and another portion of photopolymerizable composition is mixed with the biodegradable polymer, the photoinitiator and optionally the release modulating agent.

The choice of the solvent which can be used according to the present invention depends on the polarity of the therapeutic agent.

Optionally, the solvent can be selected from water, dimethyl sulfoxide, decylmethyl sulfoxide, 2-pyrrolidone, 1-methyl-2-pyrrolidne, N-vinyl-pyrrolidine, N-Methyl-2-pyrrolidone, N-ethyl-pyrrolidone, glycerol formal, glycerol, polyethylene glycol, propylene glycol, benzyl alcohol, benzyl benzoate, ethyl benzoate, triacetin, triethyl citrate, dimethylformamide, dimethylacetamide, acetonitrile, dichloromethane and tetrahydrofuran.

In one embodiment, co-solvents may be used and they can be selected from dichloromethane, tetrahydrofuran, ethyl acetate, acetone, dimethylformamide, acetonitrile, acetic acid, methanol, ethanol, isopropanol, glycofurol or butanol.

In case of hydrophilic therapeutic agents, the solvent may be an aqueous based solvent such as water or phosphate buffered saline (PBS) solution.

According to another embodiment, the solvent may be selected from dimethyl sulfoxide, decylmethyl sulfoxide, acetonitrile, 2-pyrrolidone, 1-methyl-2-pyrrolidne, N-methyl-2-pyrrolidone and glycerol formal.

Alternatively, the therapeutic agent is not dissolved into a solvent prior to mixing it with the other components. Accordingly, the therapeutic agent, the polymerizable composition, the biodegradable polymer, the photoinitiator and optionally the release modulating agent are mixed together in any order of addition. Alternatively, the therapeutic agent is first mixed with a portion of the photopolymerizable composition and another portion of photopolymerizable composition is mixed with the biodegradable polymer, the photoinitiator and optionally the release controlling agent.

Another aspect of the present invention is to provide an ocular composition as described above, for use in the preparation of an ocular implant. Alternatively, the ocular composition of the present invention is used to coat an ocular implant or a support for an ocular implant.

A further aspect of the present invention is a method of making an ocular implant comprising a step of providing an ocular composition of the present invention and, subsequently, a step of irradiating the ocular composition with light at a wavelength between 200 and 550 nm, between 200 and 500 nm, between 200 and 490 nm, or between 200 to 425 nm, for a period of time between 1 second and 60 minutes, between 30 seconds and 30 minutes, between 2.5 minutes and 20 minutes, between 5 minutes and 10 minutes. In one embodiment, the crosslinking is for 3 seconds, 6 seconds, 9 seconds, 15 seconds, 30 seconds, 1, 2.5, 5, 10, 20 or 30 minutes.

A further aspect of the present invention is an ocular implant obtainable by the method mentioned above.

In one embodiment, polymer molecular weight, type and copolymer ratio, drug type and loading, implant size, time and extent of UV crosslinking, amount and type of photoinitiator, release modulating agent, solvent and/or co-solvent can be altered to control the rate and extent of drug release. The alteration of these factors provides compositions of the invention that can be easily tailored to produce desired period of drug release to address specific clinical/patient needs in treating various ocular diseases.

The ocular compositions of the invention can be:
i) injected into the eye followed by application of short-term UV light to induce in situ photocrosslinking, resulting in implant formation, termed as In Situ Photocrosslinked Implants (ISPcI); and
ii) photocrosslinked prior to application in the eye to form an implant of desired shape and size (e.g. film, rod or nano/microparticles) that can be administered intraocularly to provide desired period of drug delivery, termed as Preformed Photocrosslinked Implants (PPcI).

Alternatively, the compositions of the invention can be used to coat ocular devices, including both in situ and pre-formed ocular devices.

The implants of the present invention can be of any desired shape such as but not limited to, rectangular, square, spherical, cylindrical, circular, oval, films, dumbbell, rods and beads.

The implants of the present invention can have any desired size and can be, for example, in the macro, micro or nano particle size range.

In one embodiment of the present invention, the ocular implant is an implant which is less than 10 mm or less than 5 mm or less than 3 mm in one of the dimensions. In one embodiment, the implant is a rectangular implant of dimensions 10×5×0.5 mm. In one embodiment, the implant (ISPcI) is a spherical implant of diameter less than 10 mm or less than 5 mm or less than 3 mm. In one embodiment of the present invention, the ocular implant is a nanoparticle or a microparticle.

In one embodiment, the nanoparticle ocular implant is less than 1,000 nm, less than 900 nm, less than 750 nm, less than 500 nm, or less than 100 nm.

In one embodiment, the microparticle ocular implant is less than 1,000 μm, less than 900 μm, less than 750 μm, less than 500 μm, or less than 25 μm.

Optionally, the implant is an in situ formed ocular implant. Alternatively, the implant is a pre-formed ocular implant.

In Situ Photocrosslinked Implants (ISPcI) according to the present invention are those that form and take up their final localized structure once they are inserted into the body. The ability of the ISPcI to fill irregular defects is one of their advantage. The ISPcIs of the present invention also have additional advantages, which include, site-specific action due to relatively easy and less invasive application, localized delivery to specific tissues, prolonged delivery times, reduction in side effects linked with systemic delivery and also superior patient comfort and compliance. An additional advantage of the ISPcIs of the present invention is that it does not require extreme pH conditions or elevated temperatures during processing, which could cause issues when working with temperature or pH labile drugs like proteins, peptides or genetic material. Furthermore, rapid crosslinking at physiological temperatures can swiftly entrap drug molecules and can result in an ISPcI that provides long-term controlled drug release. Photocrosslinking is also beneficial in comparison to spontaneous crosslinking (e.g. enzymatic, self-assembled, Michael addition) as the initiation of the process is only triggered when exposed to a light source, therefore premature gelation is not an issue resulting in excellent control of material formation. Furthermore, short-term application of UV light will not cause any safety issues as it is considered safe for ocular applications, as UV light is clinically used for corneal crosslinking. Importantly, administration by this method allows the injection of a relatively low viscosity material into the body, which then solidifies due to phase inversion and forms a semi-solid depot that upon crosslinking controls the drug delivery to provide short or long-term therapeutic action.

In one embodiment, the ISPcIs are formed by injection of an ocular composition of the present invention into a subject in need thereof and subsequent crosslinking using external source of UV light that results in formation of a solid implant which controls drug release for a desired period of time.

For ISPcIs of the invention the molecular weight of the photopolymerizable composition is typically between 100 and 6,000 Da, between 200 and 3,000 Da, or between 200 and 1,000 Da.

Preformed Photocrosslinked Implants (PPcI) of the present invention can be inserted in the eye, for example in the fornix, subconjunctively, intracameral, intrastromal/intracorneal, transsclerally/periocular, intrasclerally or intravitreally, subretinal, to treat the front of the eye or back of the eye diseases. The PPcI can be fabricated in a variety of shapes including, but not limited to, rods, films, cylindrical or circular and sizes, including in the form of micro or nanoparticles.

In one embodiment, PPcI nano and microparticles are obtained by sonicating the mixture of therapeutic agent, photopolymerizable composition, biodegradable polymer, photoinitiator and, optionally, release modulating agent in an aqueous medium. In one embodiment, the aqueous medium is a combination of water and phosphate buffered saline (PBS). Irradiation can be applied during sonication i.e. sonicating the mixture under UV light or it can alternatively occur after the sonification step.

The PPcIs of the present invention have the advantage of high crosslink density and/or a tight polymer network structure which can be configured to control drug release and/or eliminate any burst release.

The PPcIs of the present invention can be fabricated to have a single and/or multiple layer which will enable loading of more than one drug or the same drug with different release profiles or rates.

Furthermore, the rate of degradation of the implants can be slower for the PPcIs than for the ISPcIs of the invention and can be controlled in function of the specific diseases or disorders to be treated.

For the PPcIs of the invention the average molecular weight of the photopolymerizable polymers is typically between 100 and 300,000 Da, between 200 to 100,000 Da, between 200 to 50,000 Da, between 200 to 20,000 Da, or between 200 to 10,000 Da.

In one embodiment, the present invention is a PLGA/PEGDA PPcI. In another embodiment, the present invention is a PLGA/PEGDA ISPcI.

In one embodiment, the biodegradable polymer is essentially contained within a matrix of the photopolymerizable composition. Optionally, the biodegradable polymer is essentially contained within a matrix of the photopolymerizable composition that forms a gel upon mixing. In one embodiment the photopolymerizable polymer is crosslinked in presence of a photoinitiator and the biodegradable polymer and therapeutic agent(s). In one embodiment, the biodegradable polymer is hydrophobic in nature and the photopolymerizable polymer is hydrophilic in nature. In one embodiment, the degree of crosslinking of the composite implant will govern the rate and extent of release of the therapeutic agent(s).

Another aspect of the present invention relates to an ocular implant comprising at least 20% w/w of a therapeutic agent, 5 to 75% w/w of a crosslinked polymer matrix and 0.1 to 40% w/w of a the biodegradable polymer is selected from the group consisting of lactide/glycolide copolymer (including poly(lactide-co-glycolide) (PLGA)), poly (L-lactide) (PLA), polyhydroxyalkanoates, including polyhydroxybutyrate, polyglycolic acid (PGA), polycaprolactone (PCL), poly (DL-lactide) (PDL), poly (D-lactide), lactide/caprolactone copolymer, poly-L-lactide-co-caprolactone (PLC) and mixtures, copolymers, and block copolymers thereof, characterized in that a) the crosslinked polymer matrix is obtained by crosslinking a photopolymerizable composition selected from the group consisting of fragments or monomers of polyalkylene glycol mono-acrylate, polyalkylene glycol diacrylate, polyalkylene glycol methacrylate and polyalkylene glycol dimethacrylate, and mixtures, copolymers and block copolymers thereof; and b) the therapeutic agent and the biodegradable polymer are embedded in the polymer matrix.

As used herein, "embedded" means that the therapeutic agent is essentially trapped within the crosslinked polymer matrix and it is homogeneously dispersed or dissolved in the crosslinked polymer matrix and/or the biodegradable polymer.

In the compositions and implants of the present invention, varying the UV crosslinking time can control the rate of and duration of drug release. In some embodiments, an increase in UV crosslinking times causes a decrease in drug release. Additionally, varying the concentration of the photoinitiator can control the rate and duration of drug release. Furthermore, varying both the UV crosslinking time and the concentration of photoinitiator can control the rate and duration of drug release. In one embodiment, decreasing the concentration of the biodegradable polymer (such as PLGA) increases the drug release rate. In one embodiment, adding a pore-forming agent (e.g. $MgCO_3$), increases the drug release rate. In one embodiment, higher UV crosslinking time and higher concentration of photoinitiator can sustain the drug release for longer periods of time. In one embodiment, the drug release can be sustained for a period of greater than 1 day, 2 days, 1 week, 1 month, 2 months, 3 months, 6 months or 9 months.

In some embodiments, the slow degradation rate of the ISPcIs and PPcIs of the present invention provide protection of the sensitive molecules such as peptides and proteins.

In some embodiments, burst release can be eliminated or controlled by varying the UV crosslinking time and varying formulation composition, implant volume.

In one embodiment, the present invention is a PPcI with no or low burst release. In one embodiment, the present invention is a PPcI with high crosslinking density that significantly slows drug diffusion.

In one embodiment, the ocular implants of the present invention comprise the therapeutic agent in a concentration between 200 µg and 2000 µg per µm³, between 1000 µg and 2000 µg per µm³, between 1200 µg and 1800 µg per µm³, between 1200 µg and 1500 µg per µm³.

Any of the implants and compositions described herein are suitable for use in any of the methods of the invention described herein.

In one embodiment, the present invention is a method of treating a disease or disorder of the eye in a subject in need thereof, comprising administering a composition or implant of the present invention to an ocular area of the subject.

In one embodiment, the present invention is a composition or implant of the present invention for use in treating a disease or disorder of the eye in a subject in need thereof.

As used herein, an "ocular area" is an area inside, outside or adjacent to the eye of the subject. In one embodiment, the ocular area is the sclera (intrascleral), outside the sclera (transscleral), the vitreous body, the choroid, the cornea, the stroma, intracameral, the aqueous humor, the lens, the fornix, or the optic nerve.

In one embodiment, the compositions and implants can be administered by injection, including, intravitreal, subconjunctival, peribulbar, subtenon or retrobulbar injections and onto the cornea.

In some embodiments, the implants are administered via a surgical procedure. In some embodiments, the implants are secured in place, after surgical implantation, via an adhesive or sutures.

The term "subject" refers to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In another embodiment, the subject is a "human".

As used herein, the terms "treat", "treatment" and "treating" refer to therapeutic treatments includes the reduction or amelioration of the progression, severity and/or duration of a disease, disorder or condition, or the amelioration of one or more symptoms (specifically, one or more discernible symptoms) of a disease, disorder or condition, resulting from the administration of the compositions or implant of the invention. In specific embodiments, the therapeutic treatment includes the amelioration of at least one measurable physical parameter of a disease, disorder or condition. In other embodiments the therapeutic treatment includes the inhibition of the progression of a condition, either physically by, e.g., stabilization of a discernible symptom, physiologically by, e.g., stabilization of a physical parameter, or both. In other embodiments the therapeutic treatment includes the reduction or stabilization of a disease, disorder or condition.

In one embodiment, the disease, or disorder is pain, inflammation, infection, cataracts, allergies, age-related macular degeneration (AMD), diabetic retinopathy (DR), macular edema, diabetic macular edema (DME), cytomegalovirus (CMV), retinitis, retinitis pigmentosa, uveitis, dry-eye syndrome, keratitis, glaucoma, blepharitis, blepharicon-junctivtis, ocular hypertension, conjunctivitis, cystinosis, vitreomacular adhesion, corneal neovascularisation, corneal ulcers and post-surgical ocular inflammations/wound healing.

The following list of numbered items are embodiments comprised by the present invention:

1. An ocular composition comprising:
   a) at least 20% w/w of a therapeutic agent;
   b) 5 to 75% w/w of a photopolymerizable composition selected from the group consisting of fragments or monomers of polyalkylene glycol mono-acrylate, polyalkylene glycol diacrylate, polyalkylene glycol methacrylate, polyalkylene glycol dimethacrylate, and mixtures, copolymers, and block copolymers thereof.
   c) 0.1 to 40% w/w of a the biodegradable polymer is selected from the group consisting of lactide/glycolide copolymer (including poly(lactide-co-glycolide) (PLGA)), poly (L-lactide) (PLA), polyhydroxyalkanoates, including polyhydroxybutyrate, polyglycolic acid (PGA), polycaprolactone (PCL), poly (DL-lactide) (PDL), poly (D-lactide), lactide/caprolactone copolymer, poly-L-lactide-co-caprolactone (PLC) and mixtures, copolymers, and block copolymers thereof, and
   d) a photoinitiator.
2. The ocular composition according to embodiment 1, wherein the therapeutic agent is present in an amount between 20 and 70% w/w.
3. The ocular composition according to embodiment 2, wherein the therapeutic agent is present in an amount between 40 and 70% w/w.
4. The ocular composition according to embodiment 3, wherein the therapeutic agent is present in an amount between 50 and 70% w/w.
5. The ocular composition according to any preceding embodiment, wherein photopolymerizable composition is selected from the group consisting of fragments or monomers of polyalkylene glycol diacrylate, polyalkylene glycol dimethacrylate, and mixtures, copolymers, and block copolymers thereof.
6. The ocular composition according to any preceding embodiment, wherein the photopolymerizable composition is selected from the group consisting of polyethylene glycol diacrylate, diethylene glycol diacrylate, polyethylene glycol dimethacrylate, diethylene glycol dimethacrylate, polypropylene glycol diacrylate, dipropylene glycol diacrylate, dipropylene glycol dimethacrylate, and polypropylene glycol dimethacrylate or mixtures, copolymers, or block copolymers thereof.
7. The ocular composition according to embodiment 6, wherein the photopolymerizable composition is polyethylene glycol diacrylate (PEGDA).
8. The ocular composition according to any preceding embodiment, wherein the biodegradable polymer is present in an amount between 5 and 10% w/w.
9. The ocular composition according to any preceding embodiment, wherein the biodegradable polymer is lactide/glycolide copolymer (including poly(L-lactide-co-glycolide) (PLGA)), poly (L-lactide) (PLA), poly (DL-lactide) (PDL), and lactide/caprolactone copolymer (PLC).

10. The ocular composition according to embodiment 9, wherein the biodegradable polymer is poly(lactide-co-glycolide) (PLGA).

11. The ocular composition according to any preceding embodiment, wherein the photoinitiator is a hydroxyketone photoinitiator, an amino ketone photoinitiator, a hydroxy ketone/benzophenone photoinitiator, a benzyldimethyl ketal photoinitiator, a phenylglyoxylate photoinitiator, an acylphosphine oxide photoinitiator, an acyl phosphine oxide/alpha hydroxy ketone photoinitiator, a benzophenone photoinitiator, a ribityl isoalloxazine photoinitiator, or a phenylglyoxylate photoinitiator or any combination thereof.

12. The ocular composition according to embodiment 11, wherein the photoinitiator is 1-[4-(2-hydroxyethoxy)-phenyl]-2-hydroxy-2-methyl-1-propanone, 2,2-dimethoxy-2-phenylacetophenone (DMPA), diphenyl(2,4,6-trimethylbenzoyl) phosphine oxide (DPPO) or riboflavin.

13. The ocular composition according to any preceding embodiment, further comprising a release modulating agent 14. The ocular composition according to embodiment 13, wherein the release modulating agent is selected from polysaccharide, including chitosan and cellulose based materials including hydroxypropyl methylcellulose (HPMC); hyaluronic acid; poloxamer; polyether including polyethylene glycol (PEG); gelatin; polyvinylpyrrolidone; polyvinyl alcohol, lactose, maltose, glucose, mannitol, sodium chloride, magnesium carbonate, magnesium hydroxide, potassium chloride, sodium bicarbonate, ammonium bicarbonate, potassium bicarbonate, agarose, sucrose and mixtures thereof.

15. The ocular composition according to embodiment 14, wherein the release modulating agent is polyethylene glycol (PEG), hydroxypropyl methylcellulose (HPMC) or mixtures thereof.

16. The ocular composition according to any embodiment 1 to 12, wherein the composition does not contain any release modulating agent 17. The ocular composition according to any preceding embodiment for use in the preparation of an ocular implant 18. A method of making an ocular composition according to any preceding embodiment, comprising the steps of:
   a) Dissolving the therapeutic agent into a solvent to obtain a solution
   b) Mixing the solution obtained under step a) with the polymerizable composition, the biodegradable polymer, the photoinitiator and optionally the release modulating agent 19. The method according to embodiment 18, wherein the solvent is a water based solvent 20. A method of making an ocular implant, comprising the steps of:
   a) Providing an ocular composition according to any embodiment 1 to 17; and
   b) Irradiating the ocular composition with light at a wavelength between 200 and 550 nm for a period of time between 1 second and 60 minutes to form the ocular implant

21. The method according to embodiment 20, wherein the ocular composition provided under step a) is administered to an ocular area of a subject before irradiating it in accordance with step b).

22. The method according to embodiment 20, wherein the ocular implant formed under step b) is administered to an ocular area of a subject 23. An ocular implant obtainable by a method as described in any embodiment 20 to 22.

24. An ocular implant comprising at least 20% w/w of a therapeutic agent, 5 to 75% w/w of a crosslinked polymer matrix and 0.1 to 40% w/w of a biodegradable polymer selected from the group consisting of lactide/glycolide copolymer (including poly(lactide-co-glycolide) (PLGA)), poly (L-lactide) (PLA), polyhydroxyalkanoates, including polyhydroxybutyrate, polyglycolic acid (PGA), polycaprolactone (PCL), poly (DL-lactide) (PDL), poly (D-lactide), lactide/caprolactone copolymer, poly-L-lactide-co-caprolactone (PLC) and mixtures, copolymers, and block copolymers thereof, characterized in that:
   a) the crosslinked polymer matrix is obtained by crosslinking a photopolymerizable composition selected from the group consisting of fragments or monomers of polyalkylene glycol mono-acrylate, polyalkylene glycol diacrylate, polyalkylene glycol methacrylate, polyalkylene glycol dimethacrylate and mixtures, copolymers, and block copolymers thereof.
   b) the therapeutic agent and the biodegradable polymer are embedded in the polymer matrix.

25. The ocular implant according to embodiment 23 or 24 which is a macro, micro or nanoparticle.

26. The ocular implant according to any embodiment 23 to 25, wherein the therapeutic agent is present in a concentration between 200 µg and 2000 µg per $\mu m^3$ of ocular implant.

EXAMPLES

Example 1: Bevacizumab (BEZ), Molecular Weight 150 kDa 1.1 Materials

Poly(ethylene glycol) diacrylate (Mn=750, PEGDA 700), Irgacure 2959 (1-[4-(2-hydroxyethoxy)-phenyl]-2-hydroxy-2-methyl-1-propanone), phosphate-buffered saline (PBS) solution tablets and hydroxypropyl methylcellulose (HPMC, 10,000 Da) were purchased from Sigma (Dorset, UK). Poly(lactide-co-glycolide) (PURASORB® PDLG 7502A, 75:25, PLGA 75/25) was obtained from Corbion Purac Biomaterials (Gorinchem, The Netherlands).

Bevacizumab (BEZ) (Avastin®) was purchased from local pharmacy (manufactured by Roche, Switzerland; each vial consists of 100 mg BEZ in 4 mL i.e., 25 mg/ml).

1.2 Preparation of BEZ Loaded Implants 1.2.1 Preparation of PPcI Implant F18 (30% w/w BEZ and 30% w/w HPMC)

50 mg PLGA 7502 (75/25) were dissolved in 650 mg PEGDA 700 to prepare Solution A. 6 mg Irgacure 2559 were dissolved in 1 mL PBS (0.01 M, pH 7.4) to prepare Solution B. 50 mg of HPMC 10,000 Da were dissolved in 1 mL of Solution B to prepare Solution C. 52.5 mg of Solution C were put into a 2 mL Eppendorf tube. 15 mg BEZ were subsequently added to the Eppendorf tube and stirred with a stirrer bar at 250 rpm for 30 seconds. The mixture so obtained was left at 4-7° C. for 30 minutes to dissolve and it was subsequently centrifuged during 1 minute at 2000 rpm to remove air bubbles. The so obtained mixture was added with 32.5 mg of Solution A 10 μL of Solution B and subsequently stirred at 250 rpm for 30 minutes. It was then centrifuged for 1 minute at 2000 rpm to remove air bubbles and subsequently stirred at 250 rpm for another 10 minutes. The mixture finally obtained was withdrawn into a silicon tube (ID: 0.635 mm) and crosslinked using a light hammer (Light Hammer® 6, Heraeus Noblelight Fusion UV Inc., Gaithersburg, MD, USA). The intensity of the UV light (365 nm) was set as 50% and the silicone tubes were exposed to the UV light for 15 sec (5 runs). The rod shape implants were removed from the silicon tube and left to dry in vacuum at 25° C. for 4 hours. The dried implants were cut into a 5 mm length.

The obtained implants had an average diameter of 0.5 mm and a length of 5 mm.

1.2.2 Preparation of PPcI Implant F19 (50% w/w BEZ)

50 mg PLGA 7502 (75/25) were dissolved in 450 mg PEGDA 700 to prepare Solution A. 6 mg Irgacure 2559 were dissolved in 1 mL PBS (0.01 M, pH 7.4) to prepare Solution B. 62.5 μL of Solution B was put into a 2 mL Eppendorf tube. 25 mg BEZ were subsequently added to the Eppendorf tube and stirred with a stirrer bar at 250 rpm for 30 seconds. The mixture so obtained was left at 4-7° C. for 30 minutes to dissolve and it was subsequently centrifuged for 1 minute at 2000 rpm to remove air bubbles. The so obtained mixture was added with 25 mg of Solution A and subsequently stirred at 250 rpm for 30 minutes. It was then centrifuged for 1 minute at 2000 rpm to remove air bubbles and subsequently stirred at 250 rpm for another 10 minutes. The mixture finally obtained was withdrawn into a silicon tube (ID: 0.635 mm) and crosslinked using a light hammer (Light Hammer® 6, Heraeus Noblelight Fusion UV Inc., Gaithersburg, MD, USA). The intensity of the UV light (365 nm) was set as 50% and the silicone tubes were exposed to the UV light for 15 sec (5 runs). The rod shape implants were removed from the silicon tube and left to dry in vacuum at 25° C. for 4 hours. The dried implants were cut into a 5 mm length. The obtained implants had a diameter of 0.4997+/−0.002 mm and a length of 5 mm.

1.2.3 Preparation of PPcI Implant F7 (6% w/w BEZ and 4% w/w HPMC)

20 mg PLGA 7502 (75/25) were dissolved in 160 mg PEGDA 700 to prepare Solution A. 6 mg Irgacure 2559 were dissolved in 1 mL PBS (0.1 M, pH 7.4) to prepare Solution B. 80 mg of HPMC 10,000 Da were dissolved in 1 ml of Solution B to prepare Solution C.

27.5 mg of Solution C were put into a 2 mL Eppendorf tube. 3 mg BEZ were subsequently added to the Eppendorf tube and stirred with a stirrer bar at 250 rpm for 30 seconds. The mixture so obtained was left at 4-7° C. for 30 minutes to dissolve and it was subsequently centrifuged for 1 minute at 2000 rpm to remove air bubbles. The so obtained mixture was added with 45.0 mg of Solution A and subsequently stirred at 250 rpm for 30 minutes. It was then centrifuged for 1 minute at 2000 rpm to remove air bubbles and subsequently stirred at 250 rpm for another 10 minutes. The mixtures finally obtained was withdrawn into a silicon tubes (ID: 0.635 mm) and crosslinked using a light hammer (Light Hammer® 6, Heraeus Noblelight Fusion UV Inc., Gaithersburg, MD, USA). The intensity of the UV light (365 nm) was set as 50% and the silicone tubes were exposed to the UV light for 15 sec (5 runs). The rod shape implants were removed from the silicon tube and left to dry in vacuum at 25° C. for 4 hours. The dried implants were cut into a 10 mm length.

The obtained implants had an average diameter of 0.5 mm and a length of 10 mm.

1.3 In Vitro Drug Release Study (PPcI Implants F7, F18, F19)

For drug release studies, each PPcI implant F7, F18 and F19 was placed into a glass vial containing 2 ml PBS (pH 7.4, 0.05% NaN$_3$). The glass vials were placed in a static incubator at 37° C. Sampling followed by complete replacement of the PBS release medium was performed on Day 1 and weekly thereafter, i.e. Day 7, Day 14, Day 21, Day 28 and so on. All the experiments were carried out in triplicates. The concentration of released drug molecule in the PBS samples was analyzed as described below.

1.4 SEC-HPLC Method for BEZ

Analysis of bevacizumab (BEZ) samples were performed using SEC-HPLC with fluorescence detection (Agilent 1260 Infinity Quaternary System) using a Phenomenex® BioZen™ SEC-2 column (150 mm length, 4.6 mm internal diameter and 1.8 μm particle size) and a Phenomenex® BioZen™ SEC-2 0.46 mm SecurityGuard Ultra Cartridge (Phenomenex, Torrance, USA). BEZ samples were analyzed in an isocratic mode using a mobile phase of 35 mM sodium phosphate buffer (pH 6.8, 300 mM NaCl), with an injection volume of 10 μL and a flow rate of 0.5 mL/min. The column temperature was maintained at 25° C. The fluorescence detector was set at an excitation wavelength of 280 nm and an emission wavelength of 340 nm.

1.5 ELISA Method for BEZ

A sandwich ELISA technique was used to determine the bioactivity of released BEZ. The washing buffer was 0.01 M PBS with 0.05 w/w % Tween 20. The blocking buffer was composed of 0.01 M PBS, 0.05 w/w % Tween 20 and 1 w/w % BSA.

The primary coating antibody, recombinant human vascular endothelial growth factor (VEGF165) was diluted 1:5000 in 0.1 M bicarbonate buffer (pH 9.6). An aliquot (100 μL) of this recombinant human VEGF165 was dispensed into each well of a 96 well plate. The plate was covered in Parafilm® and incubated for 16 h at 4° C. The plate was then washed with washing buffer (200 μL per well) for 3 times to remove unbound antibody. Then 200 μL blocking buffer was added to each well and the plate was incubated at 25° C. for 2 h. After this, the plate was washed with washing buffer (200 μL per well) for 3 times and a 100 μL volume of BEZ sample was dispensed into each well, with each sample analyzed in triplicate and a freshly prepared standard concentration curve was plated (5-400 ng/mL), and incubated at 25° C. for 1.5 h. Then the plate was washed with washing buffer (200 μL per well) for 3 times. Following this, 100 μL of the secondary antibody—biotinylated BEGF165 antibody diluted 1:10,000 in the blocking buffer—was added to each well and incubated at 25° C. for 1 h. Then the plate was washed with washing buffer (200 μL per well) for 3 times. 100 μL Streptavidin—Horseradish Peroxidase (Strep-HRP) conjugate at the dilution of 1:5000 in PBS was dispensed into each well and the plate was incubated at 25° C. in dark for 30 min. The plate was washed with washing buffer (200 μL per well) for 3 times. To detect the antibody binding, 100 μL of substrate TMB (3,3',5,5'-tetramethylbenzidine) was added to each well and incubated at 25° C. in dark for 45 min and the reaction was stopped by adding 100 μL 4.0 M hydrochloric acid to each well. Optical density was measured at 450 nm using a FLUOstar® Omega multimode microplate reader (BMG LABTECH, Offenburg, Germany).

The following table summarizes the parameters for Implants F7, F18 and F19.

| Code | BEZ loading (w/w %) | PLGA 75/25 (w/w %) | PEGDA 700 (w/w %) | Release Modu- lating Agent (w/w %) | Implant dimen- sions (D * L) (mm) | Average daily release rate (µg) | Burst release on Day 1 (µg) * |
|------|------|------|------|------|------|------|------|
| F7 | 6% | 10% | 80% | HPMC, 4% | 0.54 * 10 | 0.03-0.31 | 0.98 (0.56%) |
| F18 | 30% | 5% | 60% | HPMC, 5% | 0.52 * 5 | 0.23-4.53 | 2.74 (0.79%) |
| F19 | 50% | 5% | 45% | NONE | 0.50 * 5 | 2.18-5.67 | 14.33 (2.72%) |

* The values in the brackets represent the released percentage of BEZ on Day 1

The therapeutically relevant concentration of BEZ is reported to be 50 ng/mL (Yu Y, Lau L C M, Lo A C, Chau Y, Injectable Chemically Crosslinked Hydrogel for the Controlled Release of Bevacizumab in Vitreous: A 6-Month In Vivo Study. Transl Vis Sci Technol. 2015; 4(2):5. Doi: 10.1167/tvst4.2.5). Considering 4 mL as the volume of human vitreous humour, the therapeutic level of BEZ in human eye is 0.2 µg. The upper limit for BEZ is 1.25 mg, i.e. 1250 µg, for one eye (Edith Poku, John Rathbone, Emma Everson-Hock, Munira Essat, Ruth Wong, Abdullah Pandor, Allan Wailoo, Bevacizumab In Eye Conditions: Issues Related To Quality, Use, Efficacy and Safety, School of Health and Related Research, University of Sheffield, August 2012).

Figure 2:
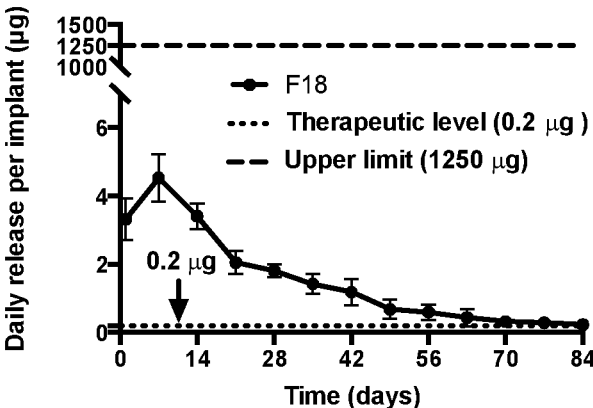
FIG. 2 Shows the in vitro release of BEZ from implant F18, expressed as daily release in μg (Mean±SD, n=3).
Figure 3:
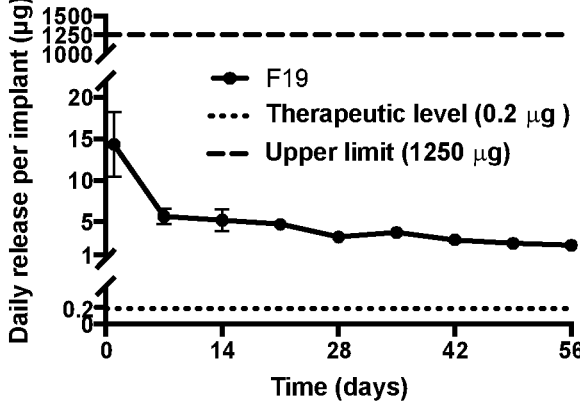
FIG. 3 Shows the in vitro release of BEZ from implant F19, expressed as daily release in μg (Mean±SD, n=3).
Figure 4:
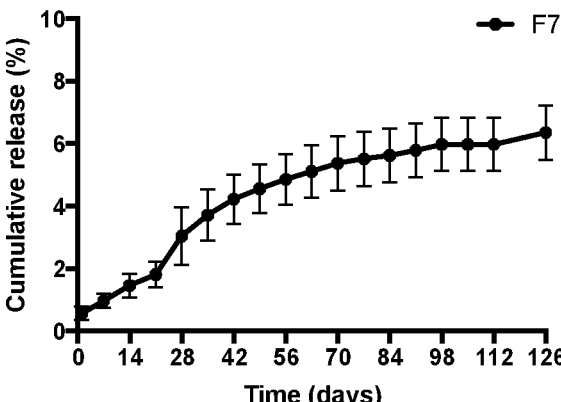
FIG. 4 Shows the in vitro release of BEZ from implant F7, expressed as percentage cumulative release (Mean±SD, n=3).
Figure 5:
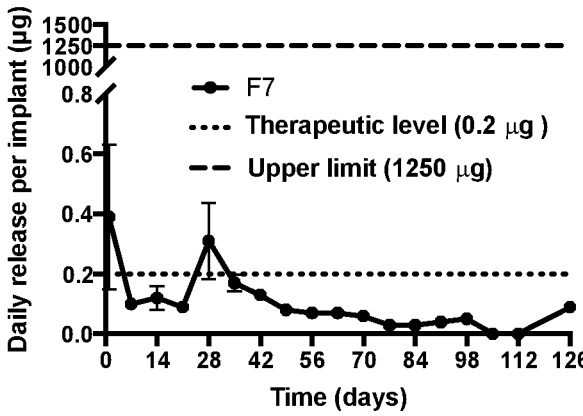
FIG. 5 Shows the in vitro release of BEZ from implant F7, expressed as daily release in μg (Mean±SD, n=3).

FIGS. 1 to 3 show that implants F18 and F19, according to the present invention, can deliver a therapeutically acceptable dose of therapeutic agent over a prolonged period of time (84 days). Implants F18 and F19 have a length which is 50% shorter than comparative implant F7 (5 mm vs 10 mm) and, accordingly, they enable to increase patient acceptance, tolerability and comfort. Moreover, the BEZ released from F18 implants maintained its bioactivity of more than 85%, as estimated by ELISA, over the period of 84 days.

Example 2 Bevacizumab Implants with Different Loading

| Formulation | BEZ loading (w/w %) | PLGA 75/25 (w/w %) | PEGDA 700 (w/w %) | Dimensions (D * L) mm |
|------|------|------|------|------|
| B1 | 10 | 5 | 85 | 0.5 * 6.5 |
| B4 | 50 | 5 | 45 | 0.5 * 6.5 |

2.1 Preparation of B1 and B4 Implants 25 mg (B1) or 50 mg (B4) PLGA 7502 (75/25) was dissolved in 425 mg (B1) or 450 mg (B4) PEGDA 700 (Sigma Aldrich, Basingstoke, UK) to prepare Solution A. 6 mg Irgacure 2959 (Sigma Aldrich, Basingstoke, UK) were dissolved in 1 mL PBS (0.01 M, pH 7.4) to prepare Solution B.

25 µL of Solution B was put into a 2 mL Eppendorf tube. 5 mg (B1) or 25 mg (B4) BEZ were subsequently added to the Eppendorf tube and stirred with a stirrer bar at 250 rpm for 30 seconds. The mixture so obtained was left at 4-7° C. for 30 minutes to dissolve and it was subsequently centrifuged for 1 minute at 2000 rpm to remove air bubbles. To the obtained mixture 45 mg (B1) or 25 mg (B4) of Solution A was added and subsequently stirred at 250 rpm for 30 minutes. It was then centrifuged for 1 minute at 2000 rpm to remove air bubbles and subsequently stirred at 250 rpm for another 10 minutes. The mixture finally obtained was withdrawn into a silicon tube (ID: 0.635 mm, Polymer System Technology, UK) and cross-linked using a light hammer (Light Hammer® 6, Heraeus Noblelight Fusion UV Inc., Gaithersburg, MD, USA). The intensity of the UV light (365 nm) was set as 50% and the silicone tubes were exposed to the UV light for 15 sec (5 runs). The rod shape implants were removed from the silicon tube and left to dry in vacuum at 25° C. for 4 hours. The dried implants were cut into 6.5 mm length.

2.2 In Vitro Drug Release Set Up

In vitro release was conducted by placing one (1) implant of B1 in an Eppendorf tube containing 1 mL of PBS (Phosphate buffered saline) with 0.05% $NaN_2$ (pH 7.4±0.2) as release media. The same in vitro release was conducted for implant B4. All the experiments were carried out in triplicate. The Eppendorf tubes containing implants were placed in an incubator and incubated at 37° C. and 0 rpm (MINI/100/F Oven, Genlab Ltd. UK). Sampling followed by complete replacement of the PBS medium was performed on Day 1, Day 3 and weekly thereafter, i.e. Day 7, Day 14, Day 21, Day 28 and so on. The concentration of released drug molecule in the PBS samples was analyzed as described in the following section.

2.3 Sample Analysis

Assay of bevacizumab was carried out on an Agilent HPLC infinity II system consisting of quaternary pump, auto-sampler, variable wavelength detector (VWD), and fluorescence detector (Agilent, UK). Separation was achieved by Phenomenex® bioZen™ SEC-2 column (1.8 µm, 4.6×150 mm) (Phenomenex, UK). The chromatographic conditions included an aqueous mobile phase composed of 35 mM sodium phosphate buffer and 300 mM sodium chloride (pH 6.8), running at a flow rate of 0.5 mL/min, and the fluorescence detector was set at excitation and emission wavelengths of 280 and 340 nm, respectively.

Figure 6:
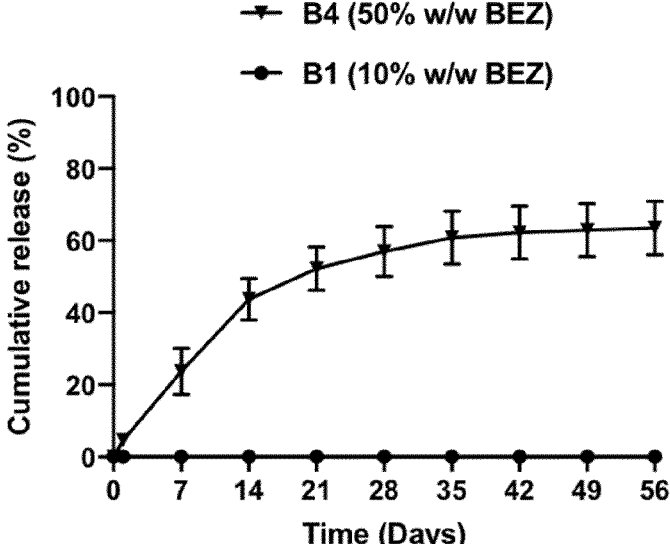
FIG. 6 Shows the in vitro release of BEZ from implants B1 and B4, expressed as percentage cumulative release (Mean±SD, n=3).
Figure 7:
FIG. 7 shows the in vitro release of BEZ from implants B1 and B4, expressed as daily release in μg (Mean±SD, n=3).
Figure 7:
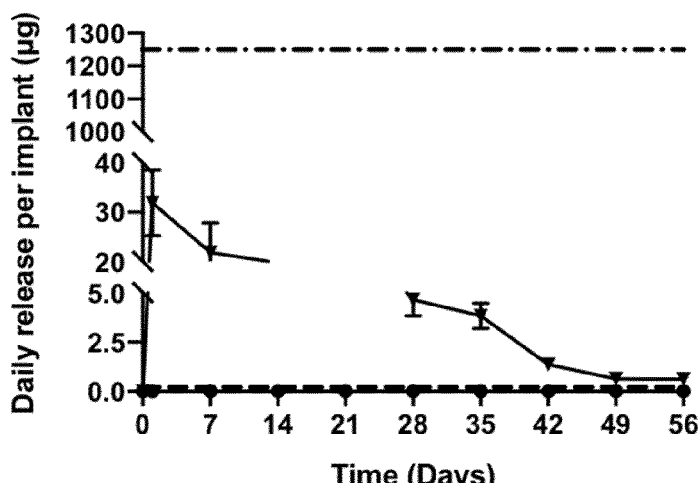

FIG. 6 and FIG. 7 show the in vitro release of B1 and B4 expressed as percentage cumulative and as daily release in µg, respectively. As it can be seen from these figures, implants B4 according to the present invention enables a sustainable release of therapeutically acceptable doses over at least 56 days, without causing unacceptable burst effects shortly after starting releasing.

Example 3 Ovalbumin, Molecular Weight 42.7 kDa

| Formulation | OVA loading (w/w %) | PLGA 75/25 (w/w %) | PEGDA 700 (w/w %) | Dimensions (D * L) mm |
|------|------|------|------|------|
| O1 | 10 | 5 | 85 | 0.5 * 7.5 |
| O2 | 20 | 5 | 75 | 0.5 * 7.5 |
| O3 | 30 | 5 | 65 | 0.5 * 7.5 |
| O4 | 40 | 5 | 55 | 0.5 * 7.5 |

3.1 Preparation of O1, O2, O3 and O4 Implants 5 mg of PLGA 7502 i.e. 75/25 (Corbion Purac Biomaterials, Gorinchem, The Netherlands) was dissolved in 85 mg (O1) or 75 mg (O2) or 65 mg (O3) or 45 mg (O4) of PEGDA 700 Da (Sigma Aldrich, Basingstoke, UK) to prepare Solution A. 5 mg Irgacure 2559 (Sigma Aldrich, Basingstoke, UK) were dissolved in 1 ml PBS to prepare Solution B. 10 mg (O1) or 20 mg (O2) or 30 mg (O3) or 40 mg (O4) albumin from chicken egg white i.e. Ovalbumin (Sigma Aldrich, Basingstoke, UK) was put into a 60 µL of Solution B in Eppendorf tube to prepare Solution C. 90 mg (O1) or 80 mg (O2) or 70 mg (O3) or 50 mg (O4) of Solution A was added to the Eppendorf tube. 60 µL of Solution C was added to the mixture slowly through Eppendorf tube wall with continuous stirring at 900 rpm for 15 minutes. The mixtures finally obtained was withdrawn into silicon tubes with ID of 0.635 mm (Polymer System Technology, UK) and cross-linked using a UV light (Light Hammer® 6, Heraeus Noble-light Fusion UV Inc., Gaithersburg, MD, USA). The intensity of the UV light was set as 50% and the silicone tubes were exposed to the UV light for 15 seconds (i.e. a total of 5 runs). The implants were then removed from the silicon tubes and left to dry in vacuum at 25° C. for 4 hours. The rod-shaped implants were cut at each 7.5 mm length.

3.2 In Vitro Drug Release Set Up

In vitro release was conducted by placing two (2) implants of O1 in a glass vial containing 2 mL of PBS (Phosphate buffered saline) with 0.05% $NaN_2$ (pH 7.4±0.2) as release media. The same in vitro release was conducted for implants O2, O3 and O4. All the experiments were carried out in triplicate. The glass vials containing implants were placed in an incubator and incubated at 37° C. and 0 rpm (MINI/100/F Oven, Genlab Ltd. UK). Sampling followed by complete replacement of the PBS medium was performed on Day 1, Day 3 and weekly thereafter, i.e. Day 7, Day 14, Day 21, Day 28 and so on. The concentration of released drug molecule in the PBS samples was analysed as described in the following section.

3.3 Sample Analysis

Analysis of Ovalbumin (OVA) in-vitro drug release samples were performed using SEC-HPLC with UV detection (Agilent 1260 Infinity Quaternary System) using a Phenomenex® Biosep-SEC-5300 column (300 mm length, 7.8 mm internal diameter and 5 μm particle size) and a Phenomenex® SecurityGuard Cartridges GFC 3000 4×3.0 mm ID (Phenomenex, Torrance, USA). 20 μL of samples were eluted with 27 mM Phosphate buffer and 150 mM NaCl pH 6.35 with flowrate of 1.0 ml/min for 14 min. Detection was carried out by UV detector at 214 nm.

Figure 8:
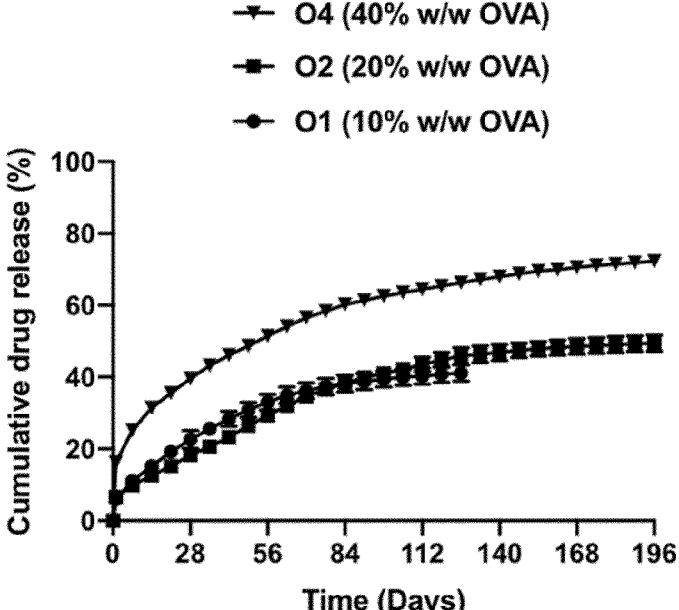
FIG. 8 shows the in vitro release of OVA from implants O1, O2 and O4, expressed as percentage cumulative release (Mean±SD, n=3).

FIG. 8 shows the in vitro release of O1, O2, and O4 expressed as percentage cumulative release.

As it can be seen from these figures, implants O2 and O4 according to the present invention enable a sustainable release of therapeutically acceptable doses over at least 196 days, without unacceptable burst effects shortly after starting to release the drug.

Example 4: Release of Bevacizumab from Different Implant Lengths

| Formulation | BEZ loading (w/w %) | PLGA 75/25 (w/w %) | PEGDA 700 (w/w %) | Dimensions (D * L) mm |
|---|---|---|---|---|
| B1 | 10 | 5 | 85 | 0.5 * 6.5 |
| BL1 | 10 | 5 | 85 | 0.5 * 10 |
| BS4 | 50 | 5 | 45 | 0.5 * 3.0 |

4.1 Preparation of BL1 and BS4 Implants

The method of preparation is the same as that of B1 and B4 implants (example 2.1) except that implant BL1 was cut into 10 mm length, while implant BS4 was cut into 3 mm length.

4.2 In Vitro Drug Release Set Up

In vitro release was conducted by placing one (1) implant of BL1 in an Eppendorf tube containing 1 mL of PBS (Phosphate buffered saline) with 0.05% $NaN_2$ (pH 7.4±0.2) as release media. In vitro release for BS4 implants was conducted by placing two (2) implants in an Eppendorf tube containing 1 mL of PBS (Phosphate buffered saline) with 0.05% $NaN_2$ (pH 7.4±0.2) as release media. All the experiments were carried out in triplicate. The Eppendorf tube containing the BL1 implant and the Eppendorf tube containing the two (2) BS4 implants were placed in an incubator and incubated at 37° C. and 0 rpm (MINI/100/F Oven, Genlab Ltd. UK). Sampling followed by complete replacement of the PBS medium was performed on Day 1, Day 3 and weekly thereafter, i.e. Day 7, Day 14, Day 21, Day 28 and so on. The concentration of released drug molecule in the PBS samples was analysed as described under Example 2.3.

4.3 Sample Analysis

The samples were analysed as under example 2.3

Figure 9:
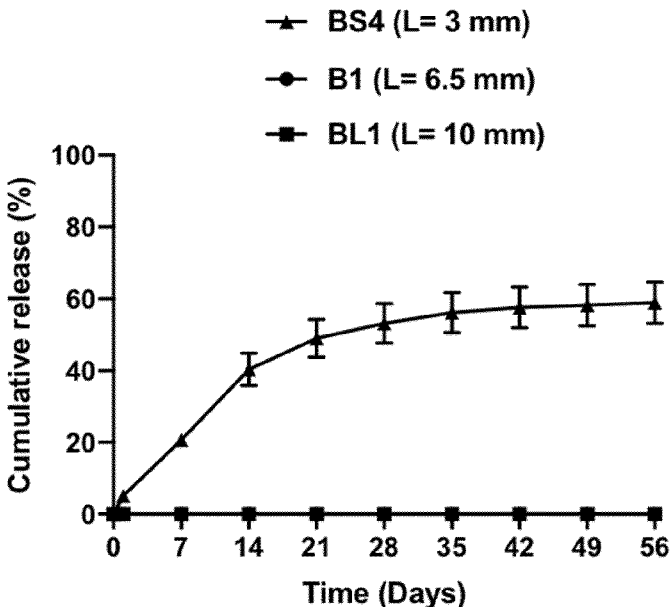
FIG. 9 shows the in vitro release of BEZ from implants B1, BL1 and BS4, expressed as percentage cumulative release (Mean±SD, n=3).
Figure 10:
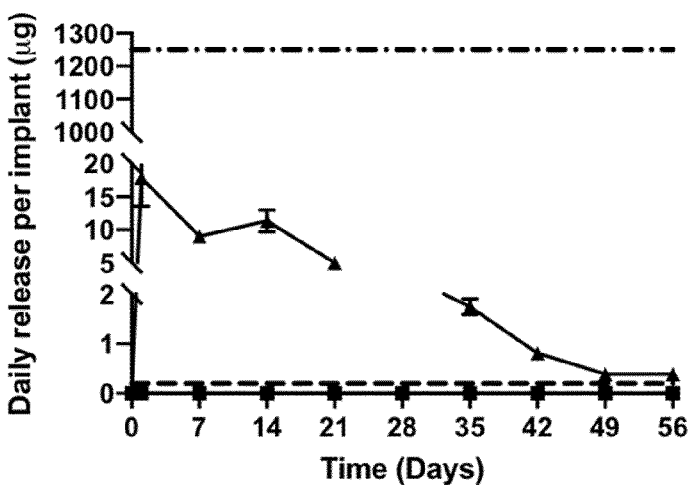
FIG. 10 shows the in vitro release of BEZ from implants B1, BL1 and BS4, expressed as daily release in μg (Mean±SD, n=3).

FIG. 9 and FIG. 10 show the in vitro release of B1, BL1 and BS4 expressed as percentage cumulative and as daily release in Mg, respectively. As it can be seen from these figures, implant BS4 according to the present invention enable a sustainable release of therapeutically acceptable doses over at least 56 days, without unacceptable burst effects shortly after starting to release the drug. BS4 is furthermore much shorter than B1 and BL1, thus substantially contributing to a better patient compliance.

Example 5: Implant Width and the Release of Bevacizumab, Molecular Weight 150 kDa

| Formulation | BEZ loading (w/w %) | PLGA 75/25 (w/w %) | PEGDA 700 (w/w %) | Dimensions (D * L) mm |
|---|---|---|---|---|
| B1 | 10 | 5 | 85 | 0.5 * 6.5 |
| BL1 | 10 | 5 | 85 | 0.5 * 10 |
| FN4 | 50 | 5 | 45 | 0.3 * 6.5 |

5.1 Preparation of FN4 Implants 50 mg PLGA 7502 (75/25) (Corbion Purac Biomaterials, Gorinchem, The Netherlands) was dissolved in 450 mg PEGDA 700 (Sigma Aldrich, Basingstoke, UK) to prepare Solution A. 6 mg Irgacure 2959 (Sigma Aldrich, Basingstoke, UK) were dissolved in 1 mL PBS (0.01 M, pH 7.4) to prepare Solution B. 62.5 μL of Solution B was put into a 2 mL Eppendorf tube and 25 mg BEZ was subsequently added.

The mixtures were stirred with a stirrer bar at 250 rpm for 30 seconds. The mixture so obtained was left at 4-7° C. for 30 minutes to dissolve and it was subsequently centrifuged for 1 minute at 2000 rpm to remove air bubbles. To the obtained mixture 25 mg of Solution A was added and subsequently stirred at 250 rpm for 30 minutes. It was then centrifuged for 1 minute at 2000 rpm to remove air bubbles and subsequently stirred at 250 rpm for another 10 minutes. The mixture finally obtained was withdrawn into a silicon tube (ID: 0.305 mm) and cross-linked using a light hammer (Light Hammer® 6, Heraeus Noblelight Fusion UV Inc., Gaithersburg, MD, USA). The intensity of the UV light (365 nm) was set as 50% and the silicone tubes were exposed to the UV light for 15 sec (5 runs). The rod shape implants were removed from the silicon tube and left to dry in vacuum at 25° C. for 4 hours. The dried implants were cut into 6.5 mm length.

5.2 In Vitro Drug Release Set Up

In vitro release was conducted by placing four (4) implants of FN4 in an Eppendorf tube containing 1 mL of PBS (Phosphate buffered saline) with 0.05% $NaN_2$ (pH 7.4±0.2) as release media. All the experiments were carried out in triplicate. The Eppendorf tubes containing implants were placed in an incubator and incubated at 37° C. and 0 rpm (MINI/100/F Oven, Genlab Ltd. UK). Sampling followed by complete replacement of the PBS medium was performed on Day 1, Day 3 and weekly thereafter, i.e. Day 7, Day 14, Day 21, Day 28 and so on. The concentration of released drug molecule in the PBS samples was analysed as described in the following section.

5.3 Sample Analysis

Figure 11:
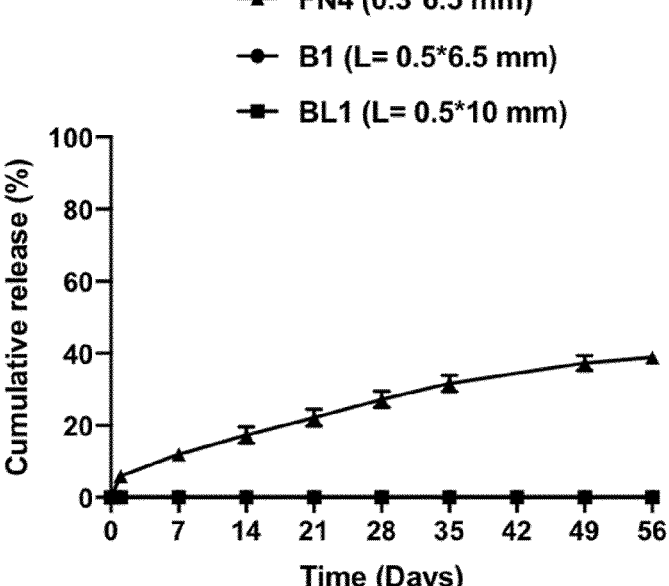
FIG. 11 shows the in vitro release of BEZ from implants B1, BL1 and FN4, expressed as percentage cumulative release (Mean±SD, n=3).
Figure 12:
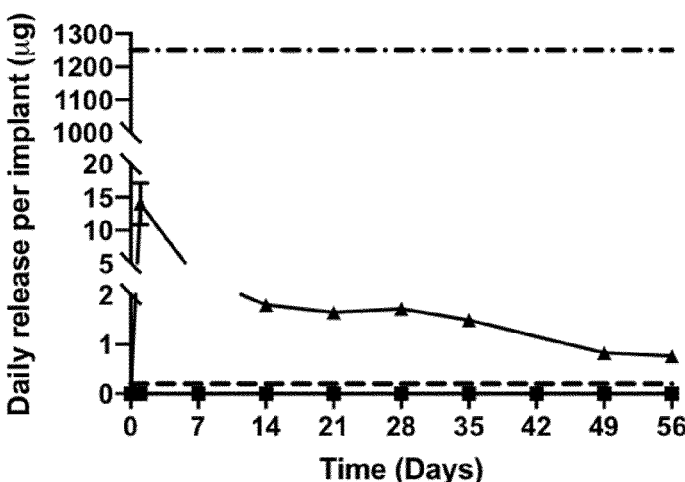
FIG. 12 shows the in vitro release of BEZ from implants B1, BL1 and FN4, expressed as daily release in μg (Mean±SD, n=3).

The samples were analysed as under example 2.3 FIGS. 11 and 12 show the in vitro release of B1, BL1 and FN4 expressed as percentage cumulative and as daily release in μg, respectively. As it can be seen from these figures, implant FN4 according to the present invention enable a sustainable release of therapeutically acceptable doses over at least 56 days, without unacceptable burst effects shortly after starting to release the drug. FN4 is furthermore much thinner than B1 and BL1, thus substantially contributing to a better patient compliance.

Example 6: Effect of Pore Forming/Release Modulating Agent on the Release of Bevacizumab, Molecular Weight 150 kDa

| Formulation | BEZ loading (w/w %) | PLGA 75/25 (w/w %) | PEGDA 700 (w/w %) | HPMC (w/w %) | Dimensions (D * L) mm |
|---|---|---|---|---|---|
| FN2 | 30 | 5 | 65 | — | 0.3 * 6.5 |
| FN5 | 30 | 5 | 60 | 5 | 0.3 * 6.5 |

6.1 Preparation of FN5

50 mg PLGA 7502 (75/25) (Corbion Purac Biomaterials, Gorinchem, The Netherlands) were dissolved in 600 mg PEGDA 700 (Sigma Aldrich, Basingstoke, UK) to prepare Solution A. 6 mg Irgacure 2959 (Sigma Aldrich, Basingstoke, UK) were dissolved in 1 mL PBS (0.01 M, pH 7.4) to prepare Solution B. 50 mg HPMC (10,000 Da) (Sigma Aldrich, Dorset, UK) was dissolved in 1 mL Solution B to prepare Solution C. 52.5 μL of Solution C was put into a 2 mL Eppendorf tube. 15 mg BEZ were subsequently added to the Eppendorf tube and stirred with a stirrer bar at 250 rpm for 30 seconds. The mixture so obtained was left at 4-7° C. for 30 minutes to dissolve and it was subsequently centrifuged for 1 minute at 2000 rpm to remove air bubbles. The so obtained mixture was added with 30 mg of Solution A and 10 μL Solution B, subsequently stirred at 250 rpm for 30 minutes. It was then centrifuged for 1 minute at 2000 rpm to remove air bubbles and subsequently stirred at 250 rpm for another 10 minutes. The mixture finally obtained was withdrawn into a silicon tube (ID: 0.305 mm) and cross-linked using a light hammer (Light Hammer® 6, Heraeus Noblelight Fusion UV Inc., Gaithersburg, MD, USA). The intensity of the UV light (365 nm) was set as 50% and the silicone tubes were exposed to the UV light for 15 sec (5 runs). The rod shape implants were removed from the silicon tube and left to dry in vacuum at 25° C. for 4 hours. The dried implants were cut into a 6.5 mm length.

6.2 In Vitro Drug Release Set Up

In vitro release was conducted by placing four (4) implants of FN5 in an Eppendorf tube containing 1 mL of PBS (Phosphate buffered saline) with 0.05% NaN₂ (pH 7.4±0.2) as release media. All the experiments were carried out in triplicate. The Eppendorf tubes containing implants were placed in an incubator and incubated at 37° C. and 0 rpm (MINI/100/F Oven, Genlab Ltd., UK). Sampling followed by complete replacement of the PBS medium was performed on Day 1, Day 3 and weekly thereafter, i.e. Day 7, Day 14, Day 21, Day 28 and so on. The concentration of released drug molecule in the PBS samples was analysed as described in the following section.

6.3 Sample Analysis

The assay of bevacizumab was carried out as described under example 2.3.

Figure 13:
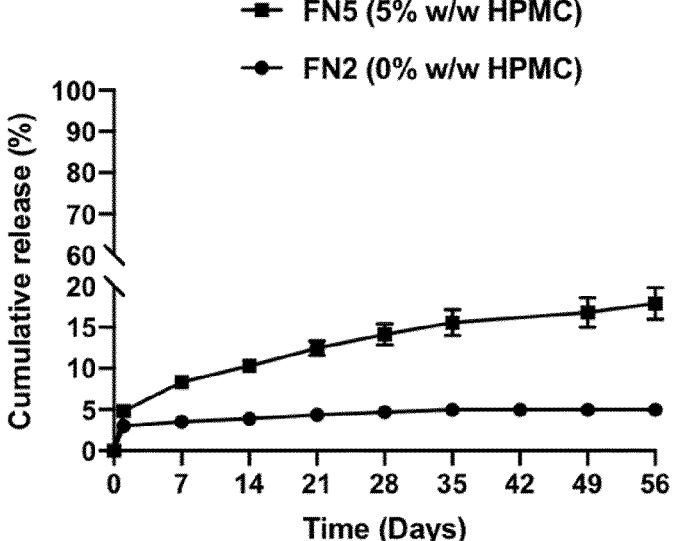
FIG. 13 shows the in vitro release of BEZ from implants FN2 and FN5, expressed as percentage cumulative release (Mean±SD, n=3).

FIG. 13 shows the in vitro release of FN2 and FN5 expressed as percentage cumulative. As it can be seen from this figure, the use of a pore forming agent further improves the release profile of the BEZ active compound over time without generating unacceptable burst releases.

Example 7: Effect of Pore Forming/Release Modulating Agent on the Release of Ovalbumin, Molecular Weight 42.7 kDa

| Formulation | OVA loading (w/w %) | PLGA 75/25 (w/w %) | PEGDA 700 (w/w %) | PEG 400 (w/w) | Dimensions (D * L) mm |
|---|---|---|---|---|---|
| O3 | 30 | 5 | 65 | — | 0.5 * 7.5 |
| O7 | 30 | 5 | 55 | 10 | 0.5 * 7.5 |

7.1 Preparation of the O7 Implant 16.7 mg of PLGA 7502 (75/25) (Corbion Purac Biomaterials, Gorinchem, The Netherlands) was dissolved in 183.3 mg PEGDA 700 Da (Sigma Aldrich. Basingstoke, UK) to prepare Solution A. 5 mg Irgacure 2559 (Sigma Aldrich. Basingstoke, UK) was dissolved in 1 ml PBS to prepare Solution B. 30 mg albumin from chicken egg white lyophilized powder i.e. Ovalbumin (Sigma Aldrich, Basingstoke, UK) was put into a 60 μl of Solution B in Eppendorf tube to prepare Solution C. 60 mg of Solution A and 10 mg of PEG400 (Sigma Aldrich, Basingstoke, UK) was added to the Eppendorf tube. 60 μl of Solution C was added to the mixture slowly through Eppendorf tube wall with continuous stirring at 900 rpm for 15 minutes. The mixtures finally obtained was withdrawn into silicon tubes with ID of 0.635 mm (Polymer System Technology, UK) and crosslinked using a UV light (Light Hammer® 6, Heraeus Noblelight Fusion UV Inc., Gaithersburg, MD, USA). The intensity of the UV light was set as 50% and the silicone tubes were exposed to the UV light for 15 seconds (i.e. a total of 5 runs). The implants were then removed from the silicon tubes and left to dry in vacuum at 25° C. for 4 hours. The rod-shaped implants were cut at each 7.5 mm length.

7.2 In Vitro Drug Release Set Up

In vitro release was conducted by placing two (2) implants of O7 in a glass vial containing 2 mL of PBS (Phosphate buffered saline) with 0.05% NaN₂ (pH 7.4±0.2) as release media. All the experiments were carried out in triplicate. The glass vials containing implants were placed in a shaking orbital incubator at a speed of 40 rpm and at 37° C. (GFL Orbital Shaking Incubator; Gesellschaft für Labortechnik mbH, Germany). Sampling followed by complete replacement of the PBS medium was performed on Day 1, Day 3 and weekly thereafter, i.e. Day 7, Day 14, Day 21, Day 28 and so on. The concentration of released drug molecule in the PBS samples was analysed as described in the following section.

7.3 Sample Analysis

Analysis of Ovalbumin (OVA) in-vitro drug release samples were performed as under Example 3.3.

Figure 14:
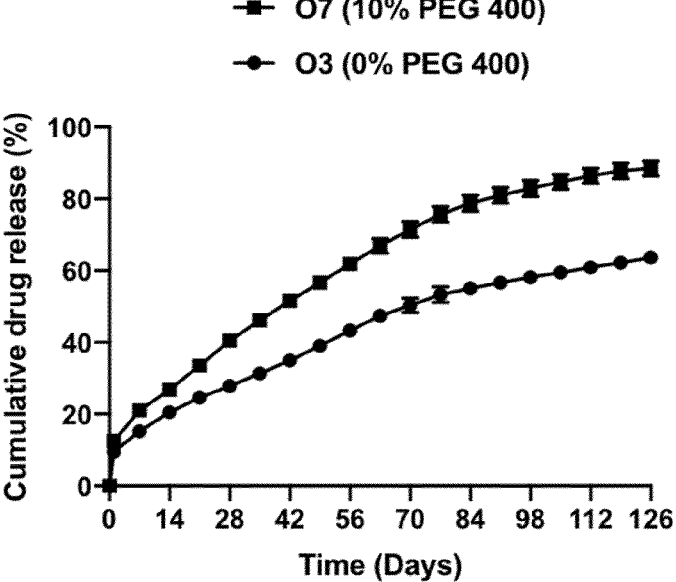
FIG. 14 shows the in vitro release of OVA from implants O3 and O7, expressed as percentage cumulative release (Mean±SD, n=3).

FIG. 14 shows the in vitro release of O3 and O7 expressed as percentage cumulative release. As it can be seen from this figure, the use of a pore forming agent further improves the release profile of the Ovalbumin over time without generating unacceptable burst releases.

The invention claimed is:

1. An ocular implant consisting of:
   a) 20% w/w to 70% w/w of a therapeutic agent, wherein the therapeutic agent comprises an antibody;
   b) 50 to 75% w/w of a photopolymerizable composition consisting of fragments or monomers of polyalkylene glycol diacrylate (PEGDA);
   c) 5% to 40% w/w of a biodegradable polymer consisting of polylactide-co-glycolide (PLGA);
   d) a photoinitiator comprising 1-[4-(2-hydroxyethoxy)-phenyl]-2-hydroxy-2-methyl-1-propanone; and
   e) a release modulating agent selected from hydroxypropyl methylcellulose (HPMC) or polyethylene glycol (PEG);
   wherein the composition, when photopolymerized to form an implant, is characterized by suppressing an initial burst release of the therapeutic agent while providing sustained release over a prolonged period greater than 1 to 9 months.

2. A method of making the ocular implant according to claim 1, comprising the steps of:
   a) dissolving the therapeutic agent into a solvent to obtain a solution; and
   b) mixing the solution obtained under step a) with the polymerizable composition, the biodegradable polymer, the photoinitiator, and the release modulating agent.

3. The method according to claim 2, wherein the solvent is a water based solvent or the solution is further mixed with the release modulating agent in step b).

4. A method of making an ocular implant, comprising the steps of:
   a) providing the ocular implant according to claim 1; and
   b) irradiating the ocular implant with light at a wavelength between 200 and 550 nm for a period between 1 second and 60 minutes to form the ocular implant.

5. The method according to claim 4, wherein the ocular implant formed under step b) is administered to an ocular area of a subject in need thereof.

6. The ocular implant according to claim 1, wherein the implant comprises a diameter of about 0.5 mm.

7. The ocular implant according to claim 1, wherein the implant comprises a length of about 8 mm.

8. The ocular implant of claim 1, wherein the antibody is bevacizumab.

9. An ocular implant consisting of:
   a) 20% w/w to 70% w/w of a therapeutic agent having a molecular weight greater than 45 kDa;
   b) 50 to 75% w/w of a photopolymerizable composition consisting of fragments or monomers polyalkylene glycol diacrylate (PEGDA);
   c) 5% to 40% w/w of a biodegradable polymer consisting of polylactide-co-glycolide (PLGA);
   d) a photoinitiator; and
   e) a release modulating agent selected from hydroxypropyl methylcellulose (HPMC) or polyethylene glycol (PEG),
   wherein the composition, when photopolymerized to form an implant, is characterized by suppressing an initial burst release of the therapeutic agent while providing sustained release over a prolonged period greater than 1 to 9 months.

10. The ocular implant of claim 8, wherein the therapeutic agent has a molecule weight of about 150 kDa.

11. The ocular implant of claim 9, wherein the photoinitiator comprises 1-[4-(2-hydroxyethoxy)-phenyl]-2-hydroxy-2-methyl-1-propanone.

* * * * *